United States Patent [19]

Liu et al.

[11] 4,344,885
[45] Aug. 17, 1982

[54] INTERMEDIATE FOR THE PREPARATION OF THIENAMYCIN

[75] Inventors: Thomas M. H. Liu, Westfield; David G. Melillo, Scotch Plains; Kenneth M. Ryan, Clark; Ichiro Shinkai, Westfield; Meyer Sletzinger, North Plainfield, all of N.J.

[73] Assignee: Merck & Co., Inc., Rahway, N.J.

[21] Appl. No.: 255,193

[22] Filed: Apr. 17, 1981

Related U.S. Application Data

[63] Continuation of Ser. No. 112,058, Jan. 14, 1980, abandoned.

[51] Int. Cl.³ ............................................. C07D 309/30
[52] U.S. Cl. .............................. 549/291; 260/245.2 T; 260/239 A; 560/37; 560/170
[58] Field of Search ........................................ 260/343.5

Primary Examiner—Norma S. Milestone
Attorney, Agent, or Firm—Frank M. Mahon; James A. Arno; Hesna J. Pfeiffer

[57] ABSTRACT

Disclosed is a process for the stereocontrolled total synthesis of thienamycin from acetone dicarboxylate via intermediate II:

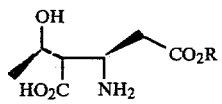

wherein R is a readily removable carboxyl protecting group.

1 Claim, No Drawings

INTERMEDIATE FOR THE PREPARATION OF THIENAMYCIN

This is a continuation of application Ser. No. 112,058 filed Jan. 14, 1980 now abandoned.

BACKGROUND OF THE INVENTION

This invention relates to a stereocontrolled total synthesis of the known antibiotic thienamycin (I).

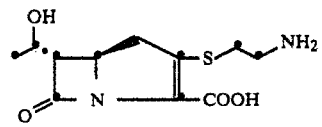

Starting from acetone dicarboxylate, the synthesis proceeds in a stereo-selective way via intermediate II:

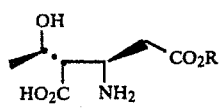

wherein R is a readily removable protecting group such as benzyl, $\beta,\beta,\beta$,-trichloroethyl, methyl, ethyl, phenyl, t-butyl and the like.

DETAILED DESCRIPTION OF THE INVENTION

The process of the present invention may conveniently be summarized by the following reaction diagram:

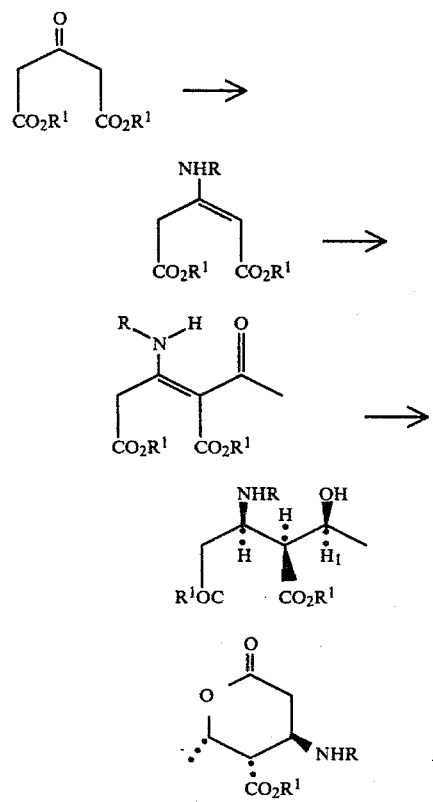

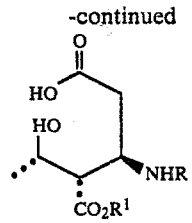

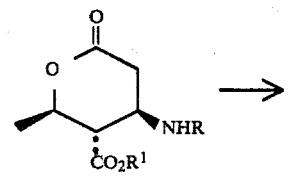

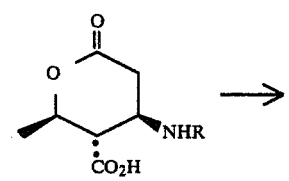

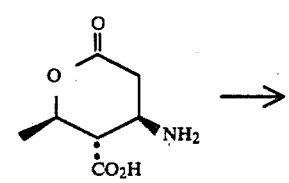

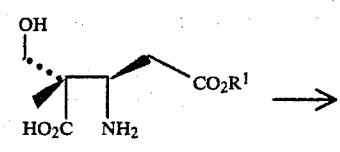

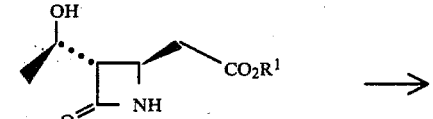

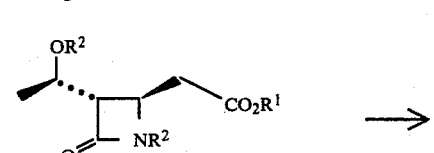

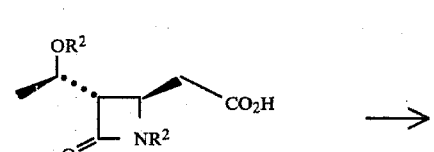

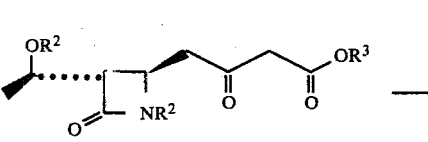

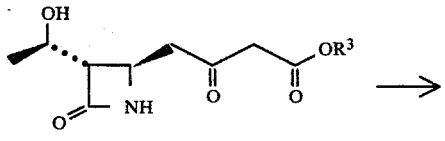

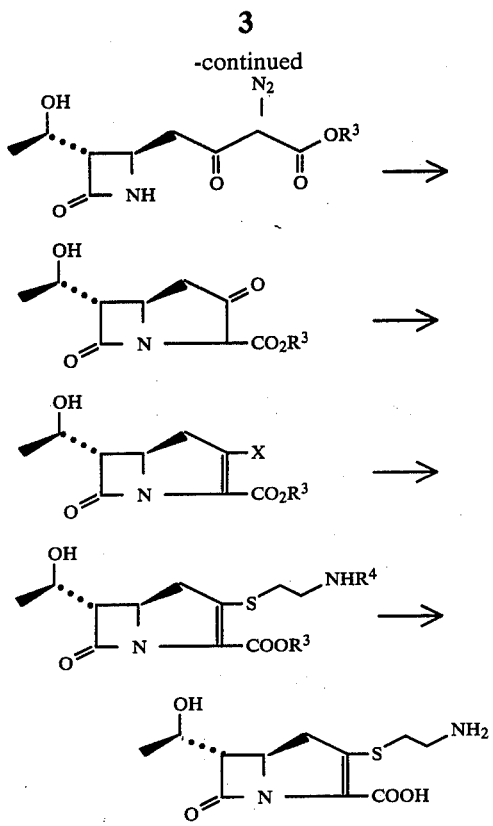

In words relative to the above reaction diagram, the acetone dicarboxylate starting material 1 ($R^1$ is alkyl having from 1–6 carbon atoms, aryl, such as phenyl, or aralkyl having from 7–12 carbon atoms) in a solvent such as toluene, methylene chloride, ethyl acetate, ether or the like is treated with an amine, $NH_2R$ (R is hydrogen; phenylalkyl having from 7–12 carbon atoms such as benzyl; 2,4-dimethoxybenzyl; alkyl having from 1–6 carbon atoms such as t-butyl; or an amine, such as α-methylbenzylamine, or the like) at a temperature of from −10° to 110° C., for from 0.5 to 24 hours. The above reaction mixture for the transformation 1→2 is conducted in the presence of a dehydrating agent such as sodium sulfate, molecular sieves, or the like.

The transformation 2→3 is accomplished by treating 2 in a solvent such as toluene, methylene chloride, ethyl acetate, ether or the like with a stoichiometric to 100-fold excess of ketene, acetic anhydride, or acetyl halide such as acetyl chloride in the presence of a base such as a triorganoamine, for example, triethylamine, at a temperature of from −10° to 95° C. for from 10 minutes to 15 hours.

The transformation 3→4 is accomplished by treating 3 in a solvent such as acetic acid, ethanol, methanol or the like at a temperature of from 0° to 80° C. with a reducing agent such as sodium cyanoborohydride, sodium borohydride, sodium acetoxyborohydride, or the like, in the presence of a carboxylic acid such as acetic, tartaric, oxalic or the like.

Cyclization of 4 to form the lactone 5 is accomplished by treating 4 in a solvent such as methylene chloride, ether, toluene, water, or the like with an acid such as hydrochloric, sulfuric, phosphoric, trifluoroacetic, or the like, at a temperature of from 0° to 100° for from 0.5 to 20 hours.

Transformation 5→6 is accomplished by treating the resulting acid addition salt of 5 in an aqueous solution of a base such as sodium hydrogen carbonate, sodium carbonate, sodium hydroxide, or the like at a temperature of from 0° to 100° C. for from 10 minutes to 48 hours. Alternatively, the free base 5 is converted to 6 by stirring an aqueous solution at from 0° to 100° C. for from 30 minutes to 48 hours.

Transformation 6→7 generates the desired isomeric configuration by reverse activation via an $SN_2$ displacement with an inversion at the carbon which will become C-8 of thienamycin. This inversion is accomplished by treating 6 in the presence of a triorganophosphine such as triphenylphosphine, tri-n-butylphosphine, or the like in the co-presence of an azodicarboxylate such as diethyl azodicarboxylate, diisopropyl azodicarboxylate, dibenzyl azodicarboxylate, or the like. Also effective to achieve the desired inversion are: triphenylphosphine and diethyl ketomalonate; or triphenylphosphine oxide and trifluoromethanesulfonic anhydride. The reaction is conducted in a solvent such as toluene, methylene chloride, tetrahydrofuran or the like at a temperature of from −10° to 50° C. for from 10 minutes to 4 hours.

Deblocking of the carboxyl group 7→8 is conveniently accomplished by mild aqueous hydrolysis in the presence of an acid such as hydrochloric, sulfuric, or the like. Typically the hydrolysis is conducted at a temperature of from 25° to 110° C. for from 20 minutes to 10 hours.

The amino deblocking transformation 8→9 is typically achieved by catalytic hydrogenation in a solvent such as acetic acid, water, or the like under a hydrogen pressure of from 40–1500 psi in the presence of a hydrogenation catalyst such as palladium on charcoal, palladium hydroxide on charcoal, platinum oxide, or the like.

The transformation 9→10 is accomplished by treating 9 with an alcohol such as benzyl alcohol, 2,2,2-trichloroethanol, methanol, phenol or the like at a temperature of from 25° to 100° C. for from 1 to 24 hours.

The value of $R^1$ is determined by the identity of the alcohol $R^1OH$ utilized (9→10). Suitable values for $R^1$ have generically been defined above relative to structure 1.

The transformation 10→11 is accomplished by treating 10 with dicyclohexylcarbodiimide (DCC), or the like in the presence of a base such as triethylamine, 4-dimethylaminopyridine, pyridine, or the like.

Alternatively, intermediate 9 may be converted directly to 11 in a single reaction by treating 9 in a solvent such as acetonitrile, acetone, nitromethane, or the like with the alcohol (benzyl, 2,2,2-trichloroethyl, methyl), the base, such as triethylamine, and the dicyclohexylcarbodiimide at a temperature of from 25° to 100° C. for from 4 to 24 hours.

Establishment of protecting group $R^2$ is accomplished by the transformation 11→12. Preferably 11 in a solvent such as dimethylformamide, ethyl acetate, methylene chloride, or the like is reacted with a reagent capable of establishing $R^2$. Preferred protecting groups are triorganosilyls such as tert-butyldimethylsilyl, or the like. Typically, protecting groups $R^2$ are established by treating 11 in a solvent such as dimethylformamide, ethylacetate, methylene chloride, or the like in the presence of a base such as pyridine, triethylamine, or the like with a stoichiometric to 4-fold excess of tert-butyldimethylsilyl chloride at a temperature of from 25° to 70° C. for from 3 to 48 hours.

It should be noted that establishment of $R^2$ is optional. The chain elongation step $\underline{13} \rightarrow \underline{14}$ (discussed below) proceeds advantageously when $R^2$ is hydrogen.

The deblocking of the carboxyl group is accomplished in the transformation $\underline{12} \rightarrow \underline{13}$. Typically the deprotection is accomplished by catalytic hydrogenation. Typically, $\underline{12}$ and the solvent such as methanol, ethylacetate, ether, or the like under a hydrogen pressure of from 1 to 3 atmospheres in the presence of a hydrogenation catalyst such as palladium on charcoal, platinum oxide, or the like is held at a temperature of from 0° to 40° C. for from 1 to 3 hours, to provide $\underline{13}$. Other deblocking procedures, such as hydrolysis, are also appropriate. Thus, for example, when $R^1$ is methyl, basic hydrolysis is preferred: Typically, this is accomplished by the addition of an equivalent amount of a base such as NaOH, KOH, Ba(OH)$_2$, Na$_2$CO$_3$, or the like to an aqueous solution of $\underline{12}$ (for eample, as the methyl ester) at 25°–100° C. for from 1.0 min. to 10 hours.

In addition $\underline{13} \rightarrow \underline{14}$ is accomplished by treating $\underline{13}$ with 1,1'-carbonyldiimidazole or the like in a solvent such as tetrahydrofuran, dimethylformamide, dimethoxyethane, or the like at a temperature of from 0° to 50° C., followed by the addition of 1.1 to 3.0 equivalents of (R$^3$O$_2$CCH$_2$CO$_2$)$_2$Mg, or the like at a temperature of from 0° to 50° C. for from 1 to 48 hours. $R^3$ is a readily removable carboxyl protecting group such as p-nitrobenzyl, o-nitrobenzyl, benzyl or the like.

The removal of the protecting groups $R^2$ is accomplished by treating $\underline{14}$ in a solvent such as 10% aqueous methanol, tetrahydrofuran, or the like in the presence of hydrochloric acid, sulfuric acid, phosphoric acid, or the like at a temperature of 0° to 50° C. for from 10 minutes to 10 hours to provide intermediate $\underline{15}$.

The diazotization reaction $\underline{15} \rightarrow \underline{16}$ is accomplished by treating $\underline{15}$ in a solvent such as ethyl acetate, methylene chloride, toluene, or the like, with a diazotization reagent such as p-toluenesulfonyl azide, p-carboxybenzenesulfonyl azide or the like in the presence of a base such as pyridine, triethylamine, or the like at a temperature of from 0° to 40° C. for from 10 to 120 minutes.

Cyclization ($\underline{16} \rightarrow \underline{17}$) is accomplished by treating $\underline{16}$ in a solvent such as benzene, toluene, THF or the like at a temperature of from 50°–110° C. for from 1-5 hours in the presence of a catalyst such as bis (acetylacetonato) Cu (II) [Cu(acac)$_2$], CuSO$_4$, Cu powder, Rh$_2$(OAc)$_4$, or Pd(OAc)$_2$. Alternatively, the cyclization may be accomplished by irradiating $\underline{16}$ through a pyrex filter (a wave length greater than 300 nm) in a solvent such as benzene, CCl$_4$, diethylether or the like at a temperature of from 0°–25° C. for from 0.5 to 2 hours. ["OAc"=acetate].

Establishment of leaving group X ($\underline{17} \rightarrow \underline{18}$) is accomplished by reacting the keto ester $\underline{17}$ with R°X such as p-toluenesulfonic acid anhydride, p-nitrophenylsulfonic acid anhydride, 2,4,6-triisopropylphenylsulfonic acid anhydride, methanesulfonic acid anhydride, toluenesulfonyl chloride, p-bromophenylsulfonyl chloride, or the like; wherein: X is the corresponding leaving group such as toluene sulfonyloxy, p-nitrophenylsulfonyloxy, methanesulfonyloxy, p-bromophenylsulfonyloxy; or other leaving groups which are established by conventional procedures and are well known in the art. Typically, the above reaction to establish leaving groups X is conducted in a solvent such as methylene chloride, acetonitrile or dimethylformamide, in the presence of a base such as diisopropylethylamine, triethylamine, 4-dimethylaminopyridine or the like at a temperature of from −20° to 40° C. for from 0.5 to 5 hours. The leaving group X of intermediate $\underline{18}$ can also be halogen. The halogen leaving group is established by treating $\underline{17}$ with a halogenating agent such as $\phi_3$PCl$_2$, $\phi_3$PBr$_2$, ($\phi$O)$_3$PBr$_2$, oxalyl chloride or the like in a solvent such as CH$_2$Cl$_2$, CH$_3$CN, THF, or the like in the presence of a base such as diisopropylethylamine, triethylamine, or 4-dimethylaminopyridine or the like. [$\phi$=phenyl.]

The leaving group X can also be a phosphate. It is typically prepared by treating $\underline{17}$ with diethyl chlorophosphate or the like in the presence of a base such as diisopropylethylamine, triethylamine, or 4-dimethylaminopyridine or the like.

The leaving group X can also be a carbonate. It is prepared by treating $\underline{17}$ with a chloroformate such as methyl, benzyl, p-nitrobenzyl or the like in the presence of a base such as diisopropylethylamine, triethylamine, or 4-dimethylaminopyridine or the like.

The leaving group X can also be an imino ester:

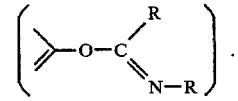

It is prepared by treating $\underline{17}$ with an imidoyl chloride such as N-phenyl trimethylacetimido chloride in the presence of a base such as diisopropylethylamine, triethylamine, or 4-dimethylaminopyridine or the like.

The reaction $\underline{18} \rightarrow \underline{19}$ is accomplished by treating $\underline{18}$ in a solvent such as dioxane, dimethylformamide, dimethylsulfoxide, acetonitrile, hexamethylphosphoramide, or the like in the presence of an approximately equivalent to excess of the mercaptan reagent HSCH$_2$CH$_2$NHR$^4$ wherein R$^4$ is hydrogen or a readily removable N-protecting group such as p-nitrobenzyloxycarbonyl, o-nitrobenzyloxycarbonyl, formimidoyl, phenoxyacetyl, phenylacetyl, 2-methyl-2-(o-nitrophenoxy)propionic, and o-nitrophenoxyacetic, or the like in the presence of a base such as sodium hydrogen carbonate, potassium carbonate, triethylamine, diisopropylethylamine, or the like at a temperature of from −40° to 25° C. for from 1 to 72 hours. The mercaptan reagent. HSCH$_2$CH$_2$NHR$^4$, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours.

The final deblocking step $\underline{19} \rightarrow I$ is accomplished by conventional procedures such as hydrolysis or hydrogenation, or enzymatically. Typically $\underline{20}$ in a solvent such as dioxane-water-ethanol; tetrahydrofuran aqueous dipotassium hydrogen phosphate-isopropanol; tetrahydrofuran-water-morpholinopropane-sulfonic acid (adjusted pH to 7.0 by adding sodium hydroxide); or the like is treated under a hydrogen pressure of from 1 to 4 atmospheres in the presence of a hydrogenation catalyst such as palladium on charcoal, palladium hydroxide, platinum oxide, or the like at a temperature of from 0° to 50° C. for from 0.5 to 4 hours to provide I.

In the foregoing word description of the above schematic reaction diagram for the total synthesis of thienamycin, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. All temperatures are in °C.

EXAMPLE 1

3-Benzylamino-2-pentenedioic acid diethyl ester (2)

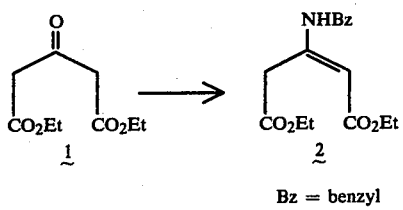

Bz = benzyl

Benzylamine (89.1 g, 0.83 moles) is added over 10 minutes to a suspension of 5 A powdered molecular sieves (270 g) and diethyl 1,3-acetonedicarboxylate 160 g) (0.79 moles) in 350 ml toluene (external cooling applied to control exotherm). The suspension is stirred at room temperature for 14–17 hours and then filtered to provide 2. The filter cake is washed with three portions of toluene. The combined filtrates may be used as is in the subsequent ketene reaction.

EXAMPLE 2

2-Acetyl-3-benzylamino-2-pentenedioic acid diethyl ester (3)

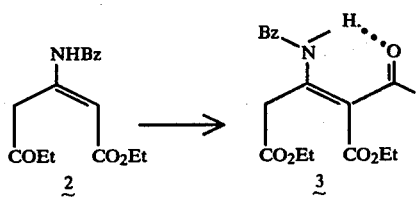

Ketene gas (generated by pyrolysis of acetone) is passed through the stirred solution of 2 (see Example 1, above) at 22° C. When starting material 2 is completely consumed (followed by TLC—solvent system 1:1 hexane/EtOAc), the solution is concentrated to give the product as a tan solid.

Yield=270.2 g (103%, purity by NMR ca 90%).

Recrystallization from ethanol affords the pure product 3 as colorless needles, mp 87°–88° C.

| Elem. anal. | | Calc. | Found |
|---|---|---|---|
| $C_{18}H_{23}NO_5$ | C | 64.85% | 64.90% |
| | H | 6.95 | 7.06 |

| Elem. anal. | | Calc. | Found |
|---|---|---|---|
| | N | 4.20 | 3.94 |

EXAMPLE 3

(2SR, 3RS)-2-[1(SR)-hydroxyethyl]-3-(benzylamino) pentanedioic acid diethyl ester 4

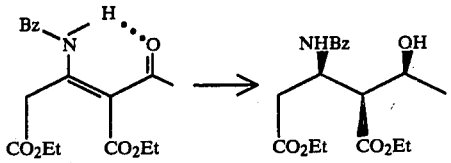

A solution of the enamine 3 (83.3 g, 0.25 mmoles) in 400 ml HOAc (acetic acid) is chilled to ca. 10° C. and sodium cyanoborohydride (20.9 g, 0.33 moles) is added as a solid portionwise over 15–30 minutes. The cooling bath is removed and the solution stirred at room temperature (22° C.) for 3.5 hours. The solution is concentrated in vacuo and the residue flushed with toluene to remove most of the acetic acid. The residue is partitioned between 400 ml EtOAc (ethyl acetate) and 300 ml saturated aqueous $NaHCO_3$. The organic layer is washed with another 300 ml portion of aqueous $NaHCO_3$. The combined aqueous layers are back extracted with 200 ml EtOAc. The organic layers are dried ($Na_2SO_4$) and concentrated in vacuo to give 4 as a colorless gum, 100 g.

EXAMPLE 4

Tetrahydro-2α-methyl-6-oxo-4β-benzylamino-2H-pyran-3α-carboxylic acid ethyl ester hydrochloride 5

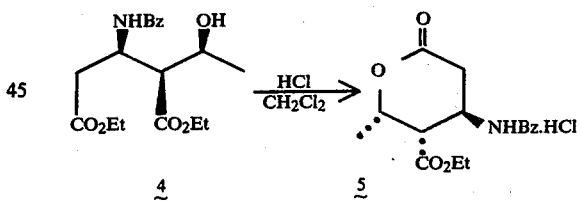

A similar batch of crude amino alcohol 4 (101.7 g) in 900 ml $CH_2Cl_2$ is treated with HCl gas (subsurface introduction) for 1 hour. The saturated solution (or suspension) is stirred at room temperature for another 2 hours. Ether (800 ml) is added to the suspension and cooled to 0° for 1 hr. The solid is collected, washed with two cold portions of $CH_2Cl_2$ and dried in vacuo to yield 5:

Yield: 26.6 g (35% from diethyl 1,3-acetonedicarboxylate) mp 181°–187° (dec).

| Elem. Anal. | | Calcd | Found |
|---|---|---|---|
| $C_{16}H_{22}ClNO_4$ | C | 58.62 | 58.95 |
| | H | 6.77 | 6.79 |
| | Cl | 10.82 | 10.94 |
| | N | 4.27 | 4.69 |

EXAMPLE 5

(2SR, 3RS)-2[1(SR)-hydroxyethyl]-3-benzylamino)-pentanedioic acid ethyl ester 6

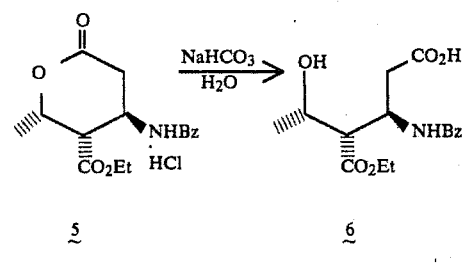

Sodium bicarbonate (11.3 g, 0.134 mole) is added to a mixture of the lactone hydrogen chloride 5 (40.0 g., 0.122 mole) in 600 ml water at 0° C. Ethyl acetate (20 ml) is added to help the stirring. The suspension is stirred at room temperature for 24 hours. The resulting solution is washed with ethyl acetate (200 ml) and then concentrated to a gum. The gum is treated with $CH_2Cl_2$, filtered to remove NaCl, and the filtrate treated with toluene until cloudy. Concentration gives the product 6 as a gum, 37.4 g (99%).

EXAMPLE 6

Tetrahydro-2β-methyl-6-oxo-4β-benzylamino-2H-pyran-3α-carboxyic acid hydrochloride 8 via the ethyl ester 7

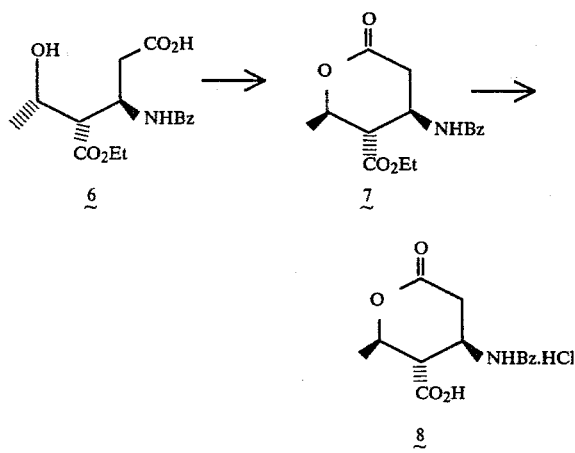

The hydroxy acid 6 (15.6 g, 0.050 moles) and triphenylphosphine (17.2 g, 0.066 moles) are dissolved in 90 ml dry tetrahydrofuran and cooled to 0°. A solution of diethyl azodicarboxylate (11.4 g, 0.066 mole) in 90 ml THF is added dropwise over 25 min. The solution is aged at room temperature for 5 hrs. and then concentrated. The crude material is slurried in 150 ml of EtOAc/hexane (1/1), filtered, and concentrated. The residue (30 g) is chromatographed on 660 g silica gel, eluting with 25% EtOAc/hexane, to provide 7 as a gum (7.63 g). Alternatively, the residue may be processed directly to the acid 8 by refluxing it in 100 ml. concentrated aqueous HCl for 3 hours. The solution is concentrated and the residue is crystallized from acetone. The product is collected by filtration, washed with acetone, and dried to give 8 as a white powder (47%).

EXAMPLE 7

Tetrahydro-2β-methyl-6-oxo-4β-amino-2H-pyran-3α-carboxylic acid hydrochloride 9

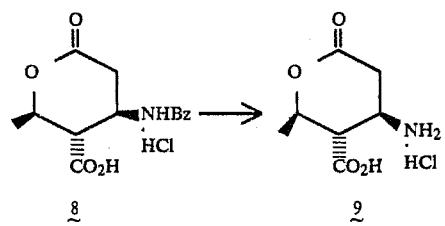

A suspension of lactone 8 (3.00 g, 0.01 mmole) and 0.50 g of 20% Pd $(OH)_2$ on charcoal in 80 ml HOAc is pressurized (40 psi) with hydrogen gas and shaken at room temperature for 24 hours. The suspension is filtered and the solid washed with two portions of MeOH. The combined filtrates are concentrated to give the product as crystalline solid. Recrystallization from HOAc gives 9 as a white powder, mp 184°–186° (dec).

| Elem Anal. | | Calcd. | Found |
|---|---|---|---|
| $C_7H_{12}ClNO_4$ | C | 40.10% | 39.95 |
| | H | 5.77 | 6.09 |
| | N | 6.68 | 6.60 |
| | Cl | 16.91 | 16.60 |

EXAMPLE 8

(2SR, 3RS)-3-amino-2[1(RS)-hydroxyethyl]-pentanedioic acid 5-benzyl ester hydrochloride

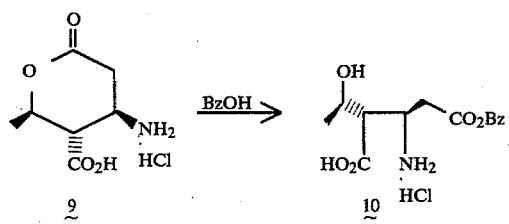

A suspension of the lactone (1.65 g, 0.0079 mmoles) in 10 ml. benzyl alcohol is heated at 70° for 1.5 hrs. The mixture is cooled to room temperature, diluted with 70 ml $CH_3CN$, and aged for 30 minutes. The product is filtered, washed with 3 portions of $CH_3CN$, and dried in vacuo to give the product 10 (2.10 g) as a white powder.

EXAMPLE 9

(3SR, 4RS)-3-[1(RS)-hydroxyethyl]-2-oxo-4-azetidineacetic acid benzyl ester

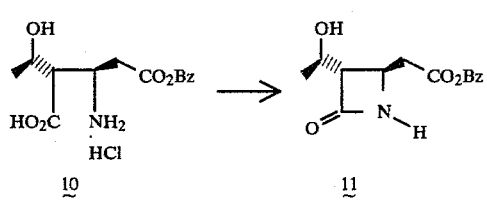

A suspension of the amino acid (2.93 g, 9.22 mmole) in CH$_3$CN (40 ml) is treated with NEt$_3$ (0.95 g, 9.39 mmole) followed by N,N'-dicyclohexylcarbodiimide (2.08 g, 10.1 mmole). The resulting suspension is aged at room temperature for 10 min. and then heated to 60° for 5 hrs. The reaction mixture is concentrated, the residue is slurried in EtOAc, and the precipitated urea is removed by filtration. The filtrate is washed successively with 1 N aqueous HCl, saturated aqueous NaHCO$_3$, H$_2$O and then dried with MgSO$_4$ and concentrated to yield 11 as a white solid. An analytical sample is prepared by recrystallization from a hexane-ethyl acetate mixture to give white needles, mp 99–101.5.

| Elem. Anal. Calcd. | | Calcd. | Found |
|---|---|---|---|
| for C$_{14}$H$_{17}$NO$_4$ | C | 63.86 | 64.05 |
| | H | 6.51 | 6.50 |
| | N | 5.32 | 5.25 |

EXAMPLE 9a (3SR, 4RS)-3-[1(RS)-hydroxyethyl]-2-oxo-4-azetidineacetic acid benzylester 11

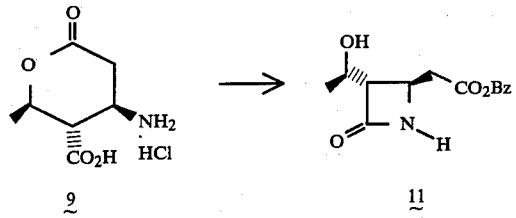

A suspension of the lactone (1.68 g, 8.0 mmole) in 10 ml. benzyl alcohol is heated to 70° for 2 hours. The solution is cooled to room temperature and a solution of NEt$_3$ (0.97 g, 9.6 mmole) in 10 ml MeCN is added followed by solid N,N'-dicyclohexylcarbodiimide (1.81 g, 8.80 mmole). The suspension is stirred at room temperature for 15 minutes then at 70° for 3.5 hours. The suspension is diluted with EtOAc, cooled to 0°, and filtered. The filtrate is washed successively with H$_2$O, 1 N aqueous HCl, H$_2$O, satd. NaHCO$_3$, H$_2$O, and then it is dried over MgSO$_4$ and concentrated in vacuo to an oily solid. The β-lactam is purified by crystallization from hexane/EtOAc or chromatography on silica gel (the product 11 is obtained as a white solid from 75% EtOAc/hexane fractions, 0.90 g).

EXAMPLE 10

(3SR, 4RS)-1-(tert-butyldimethylsilyl)-3-[1(RS)-tert-butyldimethylsilyloxyethyl]-2-oxo-4-azetidineacetic acid benzyl ester 12

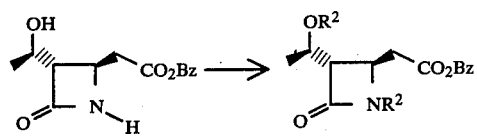

R$^2$ = —Si[C(CH$_3$)$_3$](CH$_3$)$_2$

Triethylamine (0.937 g, 9.28 mmole) in 3 ml DMF (sieve-dried) is added to the β-lactam (1.056 g, 4.01 mmol) in 15 ml DMF at room temperature. The solution is chilled to 0° and tert-butyldimethylsilyl chloride (1.39 g, 9.28 mmole) is added as a solid in 3 portions over 5 minutes. The suspension is aged at 0° for 15 minutes then at room temperature for 19 hours. The orange-brown suspension is diluted with H$_2$O and extracted with EtOAc. The organic layer is washed with H$_2$O, brine, dried and concentrated to give the product 12 as a colorless gum (2.0 g) that solidifies on standing.

EXAMPLE 11

(3SR, 4RS)-1-(tert-butyldimethylsilyl)-3-[1(RS)-tert-butyldimethylsilyloxyethyl]-2-oxo-4-azetidineacetic acid 13

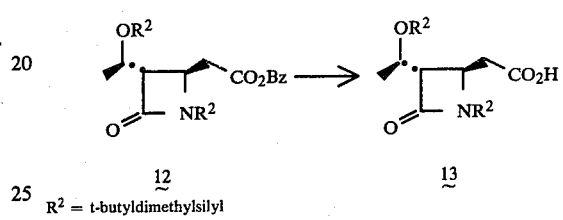

R$^2$ = t-butyldimethylsilyl

A suspension of the crude benzyl ester 12 (2.00 g, 4.01 mmole) and ½ g 10% Pd/C in 40 ml. MeOH is pressurized (40 psi) with H$_2$ and shaken for 75 minutes. The suspension is filtered and the filtrate is concentrated in vacuo to give the product 13 as a white solid, 1.60 g.

Analytical sample from EtOAc as white needles, m.p. 168°–169°

| Calcd. for | | Calculated | Found |
|---|---|---|---|
| C$_{19}$H$_{39}$NO$_4$Si$_2$ | C | 56.81 | 56.95 |
| | H | 9.79 | 9.98 |
| | N | 3.49 | 3.45 |
| | Si | 13.98 | did not analyze properly |

EXAMPLE 12

(3SR, 4RS)-1-(tert-butyldimethylsilyl)-3-[1(RS)-tert-butyldimethylsilyloxyethyl]-β,2-dioxo-4-azetidinebutanoic acid p-nitrobenzyl ester 14

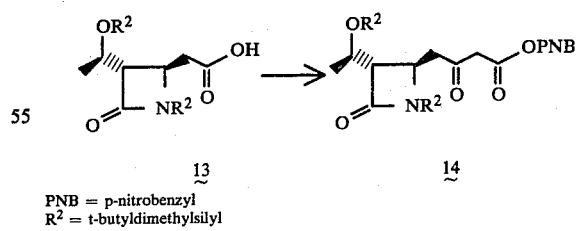

PNB = p-nitrobenzyl
R$^2$ = t-butyldimethylsilyl

To a solution of the β-lactam 13 (1.46 g., 3.62 mmole) in 30 ml. CH$_2$Cl$_2$ at room temperature is added 1,1'-carbonyldiimidazole (0.64 g., 3.95 mmole). After stirring for 30 minutes the solution is treated with 2,2-dimethyl-1,3-dioxane-4,6-dione (0.78 g., 5.43 mmole) and 4-dimethylaminopyridine (0.66 g., 5.43 mmole) and the solution aged at room temperature for another 70 hours. The solution is washed with 1 N aqueous HCl followed by H₂O and then dried with Na₂SO₄ and concentrated. The residue is dissolved in 20 ml. MeCN, p-nitrobenzyl alcohol (0.94 g., 6.15 mmole) is added, and the solution is heated to reflux for 1 hour. The reaction mixture is concentrated to a gummy solid. The pure product 14 is isolated by crystallization from isopropanol; or by chromatography on silica gel (eluent, hexane-EtOAc, 7/3).

Analytical sample from 1/1 hexane/Et₂O, colorless needles, m.p. 113.5°–115°.

| Calcd. for | | Calcd. | Found |
|---|---|---|---|
| C₂₈H₄₆N₂O₇Si₂ | C | 58.09 | 58.31 |
| | H | 8.01 | 8.25 |
| | N | 4.84 | 4.76 |
| | Si | 9.70 | did not analyze properly |

EXAMPLE 13

(3SR, 4RS)-3-(1(RS)-hydroxyethyl)-β,2-dioxo-4-azetidinebutanoic acid p-nitrobenzyl ester

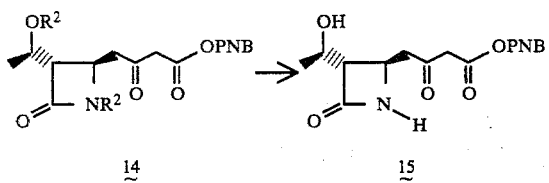

14

15

PNB = p-nitrobenzyl
R² = t-butyldimethylsilyl

Concentrated aqueous HCl (0.45 ml) is added to a suspension of the silyl derivative (0.63 g., 1.09 mmole) in 30 ml. of 10% aqueous MeOH. After stirring at room temperature for 6 hours, the solution is concentrated almost to dryness. The residue containing 15 is partitioned between H₂O and CH₂Cl₂. The organic layer is dried (MgSO₄) and concentrated to a colorless gum, 0.40 g. The crude product is used as is in the next step.

Analytical sample from hexane/EtOAc, m.p. 97°–9°.

| Calcd. for | | Calcd. | Found |
|---|---|---|---|
| C₁₆H₁₈N₂O₇ | C | 54.85 | 55.02 |
| | H | 5.18 | 5.38 |
| | N | 8.00 | 7.79 |

EXAMPLE 14

[3SR, 4RS]-α-diazo-3-[1(RS)-hydroxyethyl]-β,2-dioxo-4-azetidinebutanoic acid p-nitrobenzyl ester 16

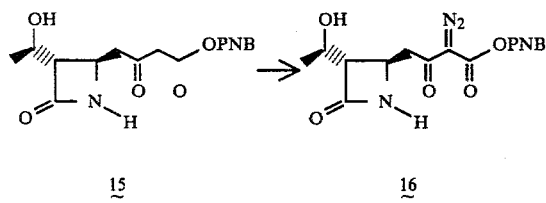

15

16

A solution of the crude β-keto ester 15 (0.83 g., 2.37 mmole) and p-toluenesulfonyl azide (0.56 g, 2.85 mmole) in 10 ml EtOAc at room temperature is treated with a solution of NEt₃ (0.31 g., 3.08 mmole) in 2 ml. EtOAc. The resulting suspension is stirred for 1 hr., chilled to 0° and filtered. The product 16 (0.77 g) is analytically pure, m.p. 160.5°–2° (dec.).

| Elem. Anal. | | Calcd. | Found |
|---|---|---|---|
| C₁₆H₁₆N₄O₇ | C | 51.06 | 51.04 |
| | H | 4.29 | 4.22 |
| | N | 14.89 | 14.76 |

EXAMPLE 15

(5RS,6SR)-6-[(RS)-1-hydroxyethyl]-3,7-dioxo-1-azabicyclo[3.2.0]heptane-2-carboxylic acid p-nitrobenzyl ester

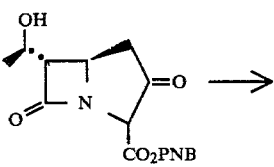

16

17

A stirred suspension of the diazo compound 16 (500 mg, 1.33 mmole) and rhodium diacetate (15 mg) in dry toluene (35 ml) is heated to 80°–5° for 2.5 hours. After filtration of the catalyst, the solution is concentrated in vacuo to give the product as a white solid, mp 92°–8°.

EXAMPLE 16

(5RS,6SR)-6-[(RS)-1-hydroxyethyl]-3-[2-(p-nitrobenzyloxycarbonyl)aminoethylthio]-7-oxo-1-azabicyclo[3.2.0]hept-2-ene-2-carboxylic acid p-nitrobenzyl ester

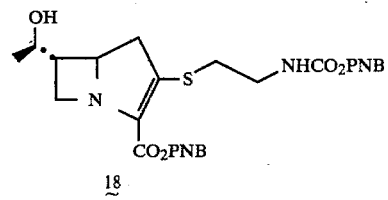

17

18

PROCEDURE A: Trifluoromethylsulfonyl Activation

To a stirred suspension of the bicyclic ketone 18 (100 mg, 0.287 mmole) in dry methylene chloride (1 ml) is added dropwise a solution of diisopropylethylamine (62 mg, 0.481 mmole) in dry CH₂Cl₂ (0.4 ml) at 0° C. under a nitrogen atmosphere. The resulting mixture is aged for 15 min. then trifluoromethanesulfonic anhydride (90 mg, 0.319 mmole) is added to give a clear solution. To the mixture is added a solution of diisopropylethylamine (250 mg, 1.94 mmole) in CH₂Cl₂ (0.3 ml) followed by N-p-nitrobenzyloxycarbonylcysteamine (77 mg, 0.30 mmole) as a solid at 0° C. The mixture is stirred for 30 min during which time the product crystallizes as a colorless solid. The solid is collected by filtration and washed with CH₂Cl₂. An additional crop of product is obtained by washing the filtrate with dilute aqueous NaHCO₃. The organic layer is dried with Na₂SO₄ and concentrated in vacuo. The residue is crystallized from EtOAC. The combined yield is 108 mg (64%) of product 18.

PROCEDURE B: Tosylate Activation

To a suspension of the bicyclic ketone 17 (50 mg, 0.144 mmole) in acetonitrile (3 ml) is added dropwise a solution of diisopropylethylamine (22 mg, 0.171 mmole) in 1 ml CH₃CN at −5° C. under a nitrogen atmosphere. After aging at this temperature for 10 min, a solution of p-toluene sulfonic anhydride (51 mg, 0.156 mmole) in 1 ml CH₃CN is added. The resulting mixture is stirred for 2 hr. at 0° C. The solution is concentrated in vacuo to a volume of approximately 1 ml and then 3 ml of dry N,N-dimethylformamide (DMF) is added and the remaining CH₃CN removed in vacuo. To the DMF solution at −5° C. is added a solution of diisopropylethylamine (40 mg, 0.31 mmole) in 0.5 ml DMF and the resulting mixture stored in a refrigerator for 70 hrs. The solution is diluted with brine and extracted with five portions of CH₂Cl₂. The combined extracts are washed with brine, dried over Na₄SO₄, and concentrated in vacuo. The residue is crystallized from an ethylacetate-ether mixture to give the product 18 as a colorless solid, 68 mg (81%).

PROCEDURE C: Phosphate Activation

To a suspension of the bicyclic ketone 17 (100 mg, 0.29 mmole) in CH₃CN (1 ml) is added dropwise a solution of diisopropylethylamine (37 mg, 0.29 mmole) in 0.4 ml CH₃CN at 0° under a nitrogen atmosphere. The resulting mixture is stirred for 15 min then a solution of diphenyl chlorophosphate (77 mg, 0.29 mmole) in 0.4 ml CH₃CN is added. The mixture is stirred for 15 min at 0° and then 15 min at room temperature. The mixture is again cooled to 0° and a solution of diisopropylethylamine (38.7 mg, 0.30 mmole) in 0.4 ml CH₃CN is added followed by N-p-nitrobenzyloxycarbonylcysteamine (77 mg, 0.30 mmole). The reaction mixture is stored overnight in a freezer, diluted with EtOAC, and filtered to give the product 18 as a colorless solid, 118 mg (70%).

EXAMPLE 17

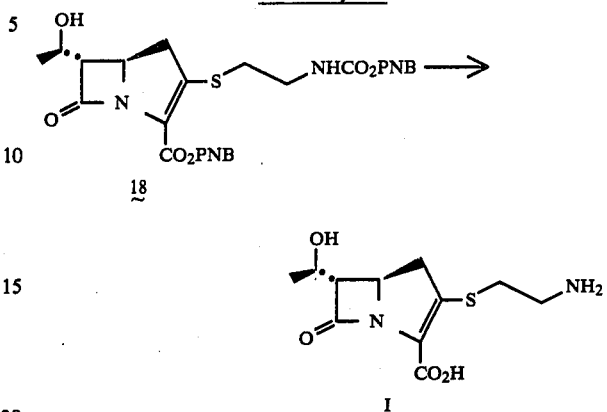

A mixture of the protected thienamycin 18 (4.9 mg, $8.362 \times 10^{-6}$ mole) and platinum oxide (3.4 mg) in tetrahydrofuran (2 ml), water (1 ml) and 0.5 M morpholinopropane sulfonic acid (adjusted to pH 7.0 by adding sodium hydroxide) (0.5 ml) is hydrogenated at 40 psi on a Parr shaker for 60 minutes. The suspension is filtered to remove catalyst and the catalyst is washed with water (2×20 ml). The filtrate is washed with EtOAC (2×15 ml). The aqueous layer is diluted to 50 ml and assayed for thienamycin. UV$\lambda_{max}$=298 mm HPLC assay 81.4% yield, retention time=298 sec., natural thienamycin 298 sec.

CROSS REFERENCE TO RELATED APPLICATIONS

The following concurrently filed, commonly assigned U.S. patent applications are similarly directed to totally synthetic schemes for the preparation of thienamycin and in that respect complement the disclosure of the present application; consequently, these applications are incorporated herein by reference.

1. U.S. patent application Ser. No. 112,020 filed Jan. 14, 1980, now abandoned.
2. U.S. patent application Ser. No. 112,021 filed Jan. 14, 1980, now abandoned.
3. U.S. patent application Ser. No. 112,035 filed Jan. 14, 1980, now U.S. Pat. No. 4,287,123.
4. U.S. patent application Ser. No. 112,057 filed Jan. 14, 1980, now U.S. Pat. No. 4,269,772.
5. U.S. patent application Ser. No. 112,022 filed Jan. 14, 1980, now U.S. Pat. No. 4,282,148.

What is claimed is:
1. A compound having the structure:

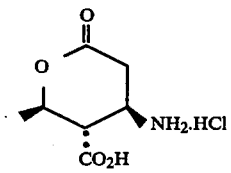

* * * * *